United States Patent [19]

Hanrahan et al.

[11] 4,292,263
[45] Sep. 29, 1981

[54] METHOD OF PRODUCING A FOAMED POLYURETHANE BODY-PROTECTING PAD

[75] Inventors: James R. Hanrahan, Fairfield, Conn.; Richard G. Levine, Lawrence, N.Y.

[73] Assignee: Zimmer USA, Inc., Warsaw, Md.

[21] Appl. No.: 69,929

[22] Filed: Aug. 27, 1979

Related U.S. Application Data

[62] Division of Ser. No. 774,377, Mar. 4, 1977, Pat. No. 4,193,134.

[51] Int. Cl.³ .............................................. B29D 27/04
[52] U.S. Cl. ........................................ 264/46.9; 2/2.7; 2/16; 2/23; 2/24; 128/149; 264/46.4; 264/257
[58] Field of Search .................... 264/45.3, 46.7, 54, 264/46.6, 46.9, 46.4, 257; 2/16, 17, 18, 19, 20, 22, 24, 23, 2.7; 128/149

[56] References Cited

U.S. PATENT DOCUMENTS

| | | | |
|---|---|---|---|
| 2,302,368 | 11/1942 | Evans | 2/94 |
| 2,626,394 | 1/1953 | Davis | 2/24 |
| 2,727,278 | 12/1955 | Thompson | 264/46.7 X |
| 3,011,494 | 12/1961 | McGowan . | |
| 3,116,196 | 12/1963 | Terry | 264/46.7 X |
| 3,136,832 | 6/1964 | Ballmer | 264/45.3 X |
| 3,189,919 | 6/1965 | Chase . | |
| 3,239,584 | 3/1966 | Terry et al. | 264/46.7 |
| 3,246,059 | 4/1966 | Moroni et al. | 264/54 X |
| 3,256,882 | 6/1966 | Huber | 2/16 X |
| 3,273,179 | 9/1966 | Ridenour | 264/46.7 X |
| 3,322,118 | 5/1967 | Sotherlin . | |
| 3,446,880 | 5/1969 | Enicks | 264/54 X |
| 3,493,449 | 2/1970 | Krug | 264/45.3 X |
| 3,606,614 | 9/1971 | Dimitroff | 2/20 X |
| 3,648,291 | 3/1972 | Pankers . | |
| 3,670,725 | 6/1972 | Gaylord . | |
| 3,858,379 | 1/1975 | Graves et al. . | |
| 3,990,440 | 11/1976 | Gaylord . | |
| 4,003,113 | 1/1977 | Bulloch | 264/46.7 X |

*Primary Examiner*—Philip Anderson
*Attorney, Agent, or Firm*—James J. Burke, II

[57] ABSTRACT

For both orthopedic and sports uses, a foamed plastic pad is integrally molded to a fabric. More particularly, a knitted sleeve is constructed having a terry loop on the interior surface of a hydrophobic yarn (e.g. acrylic) and an exterior surface of a hydrophilic yarn (e.g. cotton), whereby moisture is wicked away from the surface in a hydrokinetic fashion. A soft, hydrophilic polyurethane foam pad, which acts as a sponge, absorbs the moisture, is molded integrally with the sleeve, leaving the terry loops free for skin contact. For sports uses, knitted or woven fabrics may be employed, and stiffer, polyurethane foams are preferred.

4 Claims, 5 Drawing Figures

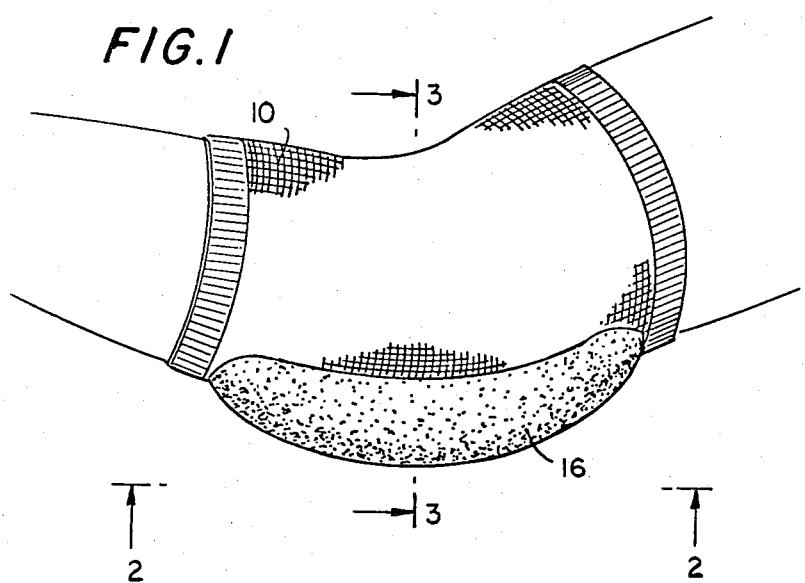
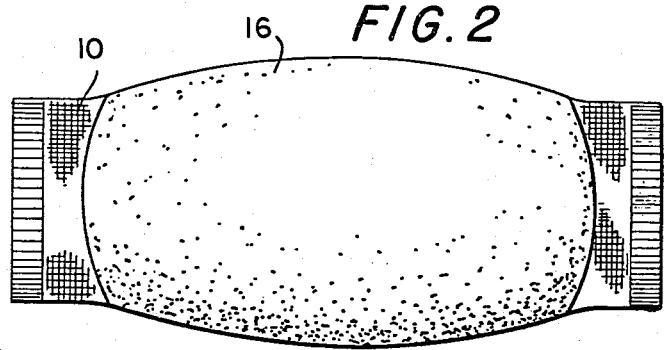
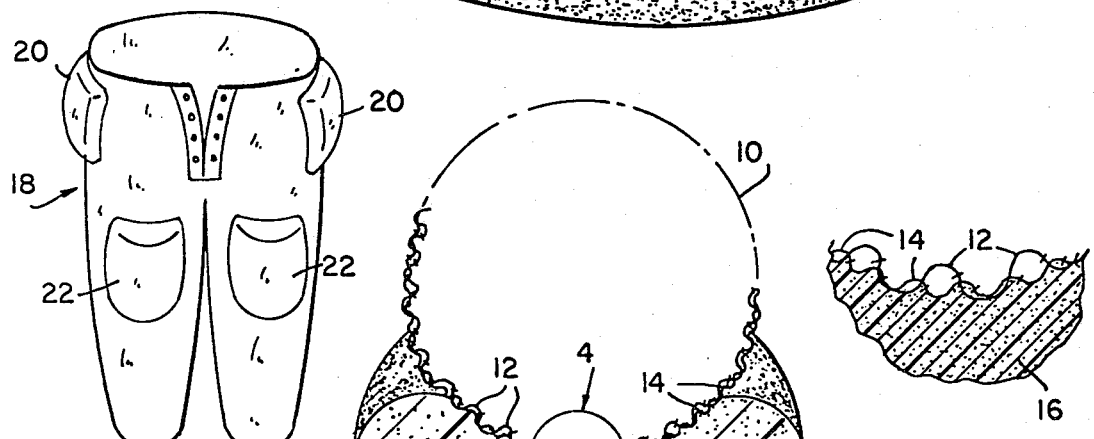

METHOD OF PRODUCING A FOAMED POLYURETHANE BODY-PROTECTING PAD

This is a division, of application Ser. No. 774,377, filed Mar. 4, 1977 now U.S. Pat. No. 4,193,134 issued Mar. 18, 1980.

BACKGROUND OF THE INVENTION

The present invention relates generally to human protective devices. In one aspect, it relates to pads that may be applied to the heels or elbows of bed-ridden patients for either the prevention or treatment of decubitus ulcers, e.g. bed sores. In another aspect, the invention relates to sports medicine, including integrally molded protective padding of controllable density and stiffness.

Bed sores are caused by friction of the heel or elbows on the bed sheet, in the presence of (body) heat and moisture, e.g. perspiration. While products are known for treatment of this painful condition, it is not believed that there has heretofore been a product effective in its prevention. What is needed is a medium that removes excess moisture from the area, allows for air circulation for removal of heat, and minimizes pressure. Of course, after an ulcer has formed the same conditions are needed for treatment, but in this case the problem of moisture removal is much more severe, because in addition to perspiration there are the inflammatory-response fluids: blood, puss, serous fluids, etc.

As pointed out in detail hereinbelow, a feature of the present invention is the direct molding of a pad to a fabric with the production of an integral product. With proper selection of materials, this product is not only washable but can also be autoclaved. With this in mind, attention was directed to sports padding.

In football, for instance, shoulder pads are separate, bulky devices of considerable weight, and discrete hip and thigh pads are inserted in special pockets in trousers. All of this adds to the weight and adds very substantially to the expense of such outfits. Because pads in accordance with the present invention are washable and of controlled properties, it is now possible to produce a jersey with integral, washable shoulder pads and trousers with similar hip and thigh pads, eliminating the special pockets, much weight and much expense, while at the same time carrying out the protective function as well or even better than conventional devices (pads of this type can not be left on the locker room floor).

PRIOR ART

In U.S. Pat. No. 3,322,118 there is disclosed a protective heel or elbow sleeve including a knitted double-layered sleeve having a generally circular, cup-shaped foam pad therebetween and cemented to the inside of the outer layer. The pad reduces pressure and the inner layer can move with the patient, reducing friction.

A commerical product on the market is much simpler. Under the trademark "Heelbo", it includes an Acrilan (TM) sleeve with an inner, bar-tacked pad shaped in the same manner as a brassiere pad and, indeed, resembling same.

By virtue of their shaped pads, these devices are improvements over earlier cushion protectors, such as is disclosed in U.S. Pat. No. 3,189,919, where a flat pad is bent around the desired area.

In U.S. Pat. No. 3,990,440 a method is disclosed involving a shaped foam pad and a separate tubular sleeve, the pad comprising adhesively bonded particles of a polyurethane foam.

U.S. Pat. No. 3,648,291 discloses a foam rubber pad within a sleeve of a hard-surfaced fabric, and including an elasticized cuff. Other devices, with variously shaped pads and securing straps, are disclosed in U.S. Pat. Nos. 3,011,494; 3,693,619; and 3,670,725. A polyvinyl alcohol gel pad is disclosed in U.S. Pat. No. 3,858,379.

OBJECTS OF THE INVENTION

A general object of the present invention is to provide an improved process for producing a protective pad for medical and athletic purposes.

Another object of the present invention is to provide an improved process for producing a pad for both prevention and treatment of decubitus ulcers.

A further object of the present invention is to provide an improved process for producing a protective pad including hydrokinetic moisture removal.

A still further object of the present invention is to provide an improved process for producing a protective pad which is less expensive to manufacture than products previously available.

Yet another object of the present invention is to provide an improved process for producing an integral protective pad and fabric combination that is not only washable but that also can be autoclaved.

A still further object of the invention is to provide a process for producing athletic wear having integral padding that is washable, lighter and less expensive than uniform-padding combinations heretofore available.

Various other objects and advantages of the invention will become clear from the following description of embodiments thereof, and the novel feature will be particularly pointed out in connection with the appended claims.

THE DRAWINGS

Reference will hereinafter be made to the accompanying drawings, wherein:

FIGS. 1 and 2 are side and bottom elevations of an embodiment of the invention;

FIG. 3 is a cross-sectional elevation along line 3—3 of FIG. 1;

FIG. 4 is an enlargement of circled area 4 in FIG. 3; and

FIG. 5 shows athletic trousers including the invention.

DESCRIPTION OF EMBODIMENTS

The present invention is based, in one aspect, on the use of hydrokinetic fabric combinations in medical and athletic applications. The hydrokinetic principle is not novel per se and, indeed is the principle employed in disposable diapers and some other products. In general, a hydrophobic material forms the surface of a fabric that is adapted to be placed next to the moisture source, and a hydrophilic material forms the opposed surface. In the former category, synthetic fibers such as acrylics are preferred, and cotton is typical of the latter.

Being hydrophobic, the acrylic will wick moisture away from the surface by capillary action and into contact with the hydrophilic cotton, where it is absorbed and migrates outwardly, facilitating evaporation and evaporative cooling. In the present invention, the integral pad also plays a role in the hydrokinetic action, as described hereinbelow.

The invention will first be described with reference to an orthopedic pad, and attention is directed to the drawings. A terry knit tube 10 is provided including Creslan (TM) terry loops 12 on the inner surface and an outer surface 14 of a cotton yarn. To provide better stretching qualitites to the sleeve, it is preferred that the cotton side include two feeds, one of cotton and one of texturalized nylon.

For example, sleeve 10 can be produced on a conventional 108 needle 4 inch cylinder machine (Carolina Knitting Machine Knitfast 4 T). For the terry loop feed Creslan acrylic type 67A (Count 1/22.5) is used; for the first back side feed type 66 texturalized nylon (Count 100/2/34), and for the second back feed cotton (Count 18/1 C.P.) is used.

It is to be noted that a sleeve as described above, e.g. hydrokinetic, forms an essential part of the invention for medical purposes. In athletic embodiments, such a fabric would be very desireable, for instance, in hockey uniforms, but would be heavier than desired for warm weather sports.

The integral foam pad 16 forms the second part of the invention. The preferred foam material, for medical applications, is a hydrophilic polyurethane polymer, though other materials can be used.

A preferred foam pad formulation is as follows: One feed is the TDI pre-polymer (Hypol 3000, Grace Chemical). The other feed is a water solution, with the following additives:

| | |
|---|---|
| surfactant (Bridge 72, ICI Americana) | 2% |
| Catalyst (Thancat DD, Jefferson Chemical) | 0.5% |
| colorant (Calotone Blue, 50% solids, American Cyanamid) | 0.5% |

The purpose of the surfactant is to optimise cell structure, and an acceptable range is 1-5%. Acceptable range for the catalyst, a tertiary amine, is 0.5 to 1.5%. The colorant is of course optional. An increase in the catalyst will speed the reaction.

The TDI pre-polymer and the aqueous solution are mixed in a ratio of from 5:5 to 5:3. With the lesser proportion of solution (5:4 or 5:3) the reaction is speeded, since water acts as a heat sink. However, certain other properties are also affected. As noted hereinbelow, this ratio also affects mold design, and it is preferred to establish one ratio. The 1:1 ratio provides very fast demold times (2 minutes) and has been used.

While density of the foam is primarily a matter of the formulation utilized, it can be varied by a factor of 2 or 3 by merely overpacking the mold. Obviously, metal molds are preferred to prevent flashing and produce a good quality skin.

Good pads have also been produced with Witco FO 538 TDI in a ratio of 100:165 with a polyol, but in this instance de-mold time was about 8 minutes.

Other foam systems—PVC, rubber latex, polyethylene, polypropylene, styrene or polyester—could be employed, but processing is quite different and properties would also be different.

Using the preferred system noted above, pads are produced having the following properties:

| | |
|---|---|
| Density | 6-7 lbs/ft$^3$ |
| ASTM 1564 | |
| Indentation Load Deflection (I.L.D) | |
| 25% | 20 lbs/50 in$^2$ |
| 65% | 57 lbs/50 in$^2$ |
| Sag factor: 2.85 | |
| Compression Load Deflection (C.L.D) | |
| 25% | 0.2 psi |
| 65% | 0.64 psi |

Forming of the pad 16 integrally with the sleeve 10 is carried out in the following manner: Pour molding is used. A mixing head is located above the molding station. [It will be appreciated that, for economic, volume production a machine including a plurality of molds arranged in a carousel is preferred.] A predetermined quantity of the mixed reactants is poured into the female mold.

Those skilled in the art will appreciate that temperature control is desireable both in terms of uniformity of product and maximum production rates. In the preferred system set forth above about 115° F. on the prepolymer side and anywhere from room to 90° F. on the solution side should be maintained. The exact temperature is not important, but uniformity of temperature is. It is also desireable to have a mold preheat station ahead of the mold station, where an 80°-85° F. temperature is established.

The female mold is of the desired shape for heel, elbow or other applications, e.g. generally cup-shaped. In the preferred system, about 40-50% shrinkage occurs after de-mold (due to water evaporation), so the mold must be appropiately oversized, and shrinkage will vary with the pre-polymer-solution ratio, so this should be kept constant.

It has been determined that, after pouring, a delay of a few seconds (less than 5) in closing the mold is useful; it is believed that gel formation commences in this period and assists in obtaining the desired degree of penetration of foam into the fabric.

The male mold is hinged behind the female, and has sleeve 10 stretched thereover. Hooks on the male mold can be used to hold sleeve 10 at the desired taughtness. Since the degree of tautness will also affect penetration, in any particular system some experimentation is required to optimise this factor. It is desired to have the backing material embedded in and integral with the pad, but the terry loops free-standing (FIG. 4).

After pouring and the (optional) delay noted hereinabove, the mold is closed and the molds are indexed to the next station. De-mold proceeds after the prescribed interval.

An important aspect of the present invention is that foams of the type described are themselves very hydrophilic; indeed they are sponge-like. They thus assist greatly in drawing moisture away from the skin and through sleeve 10. With an average pad 16 thickness of about one inch, absorbing capacity of the pad 16 is great. It will also be noted that a single layer sleeve is essential to proper hydrokinetic functioning, which contrasts with prior art devices where a double layer is either necessary or desired.

A further aspect of the invention is the method of pour molding to obtain the integrally bonded product. According to the manufacturer ("Hypol-Laboratory Procedures and Foam Formulations") it should be possible to coat or impregnate a fabric with the prepolymer, and then immerse it in water or steam for in situ foaming, something said to be not possible with other urethanes. It is thus considered surprising that an integrally bonded product can be produced by pour molding with pre-mixed ingredients.

While not wishing to be bound to any particular theory of operation, it is believed that the substantial amount of water in the formulation wets the cotton (hydrophilic) yarn on contact, thus facilitating penetration of the foam and formation of a truly integral product. Wetting is also enhanced, of course, by the surfactant.

In athletic applications, partial penetration of the pad into the material may or may not be desired. With woven fabrics, full penetration is perfectly satisfactory. Since impact absorbing properties are paramount in sports padding, somewhat stiffer pads are desired. Typical of these are an integral skin, medium density, semi-rigid urethane. In certain applications (e.g. shoulder pads) these may be provided with a rigid (pre-molded) core; otherwise, procedures would be as described hereinabove.

FIG. 5 shows a pair of football trousers 18 having integrally molded hip pads 20 and thigh pads 22.

Varous changes in the details, steps materials and arrangements of parts, which have been herein described and illustrated in order to explain the nature of the invention, may be made by those skilled in the art within the principle and scope of the invention as defined in the appended claims.

What is claimed is:

1. The method of producing a body-protecting pad comprising:
   stretching a hydrokinetic fabric sleeve over a male mold, the tautness of said stretched fabric sleeve being controlled to facilitate wetting and penetration of foam into the exterior of said fabric;
   mixing a water-foamable hydrophilic polyurethane prepolymer and water in desired proportions in an open female pad mold of desired shape;
   closing said molds; and
   demolding the resulting, integrally molded pad and sleeve.

2. The method as claimed in claim 1, wherein said water contains a surfactant and a tertiary amine catalyst.

3. The method as claimed in claim 1, wherein said closing is delayed no more than about 5 seconds after said charging.

4. The method as claimed in claim 1, wherein said sleeve is a knit terry fabric having interior, hydrophobic terry loops and a hydrophilic exterior.

* * * * *